United States Patent [19]

Debarre et al.

[11] 4,005,212

[45] Jan. 25, 1977

[54] IMIDAZO[2,1-b]THIAZOLE DERIVATIVES

[75] Inventors: Francois Debarre, Antony; Claude Jeanmart, Brunoy; Pierre Edouard Simon, Hauts-de-Seine, all of France

[73] Assignee: Rhone-Poulenc S.A., Paris, France

[22] Filed: May 12, 1975

[21] Appl. No.: 576,297

Related U.S. Application Data

[62] Division of Ser. No. 419,900, Nov. 28, 1973.

[30] Foreign Application Priority Data

Nov. 30, 1972 France .............................. 72.42580
Nov. 2, 1973 France .............................. 73.35158

[52] U.S. Cl. .......................... 424/270; 260/306.7 T
[51] Int. Cl.² ..................................... A61K 31/425
[58] Field of Search .............. 260/306.7 T; 424/270

[56] References Cited

UNITED STATES PATENTS 3,759,937  9/1973  Baklien et al. .............. 260/306.7 T Primary Examiner—Stanley J. Friedman
Attorney, Agent, or Firm—Stevens, Davis, Miller & Mosher

[57] ABSTRACT

Imidazo[2,1-b]thiazoles carrying in the 2-position a phenyl radical unsubstituted or substituted by one or two atoms or radicals selected from halogen atoms and alkyl, alkoxy, alkylthio, dialkylamino, dialkylsulphamoyl, nitro, cyano and trifluoromethyl radicals or carrying in the 2-position a 2-, 3- or 4-pyridyl radical unsubstituted or substituted by an alkyl or alkoxy radical, are new compounds possessing pharmacological properties and useful, in particular, as anti-depressants and psycho-energisers.

1 Claim, No Drawings

IMIDAZO[2,1-b]THIAZOLE DERIVATIVES

This is a division of application Ser. No. 419,900 filed Nov. 28, 1973.

This invention relates to new therapeutically useful imidazo[2,1-b]thiazole derivatives, to a process for their preparation and to pharmaceutical compositions containing them.

The new imidazo[2,1-b]thiazole derivatives of the present invention are those of the general formula:

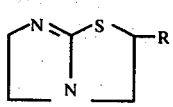
I wherein R represents a phenyl radical unsubstituted or substituted by one or two atoms or radicals, which — when two substituents are present - may be the same or different, selected from halogen atoms and alkyl, alkoxy, alkylthio, dialkylamino, dialkylsulphamoyl, nitro, cyano and trifluromethyl radicals, or R represents a 2-, 3- or 4-pyridyl radical unsubstituted or substituted by an alkyl or alkoxy radical, the alkyl radicals and alkyl moieties of other radicals containing 1 to 4 carbon atoms, and acid addition salts thereof.

The compounds of general formula I can exist in optically active forms and the invention includes optically active isomers of the imidazo[2,1-b]thiazole derivatives of general formula I and mixtures thereof, more particularly the racemic form.

According to a feature of the invention, the compounds of general formula I are prepared by the cyclisation of an imidazolidine-2-thione of the general formula:

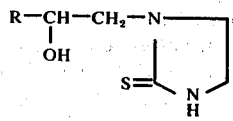
II (wherein R is as hereinbefore defined) in an acid medium. The cyclisation is generally carried out by heating a compound of general formula II in the presence of a strong inorganic acid, such as hydrochloric acid in aqueous solution or polyphosphoric acid.

The imidazolidine-2-thione derivatives of general formula II can be obtained by reacting carbon disulphide with an ethylenediamine derivative of the general formula:

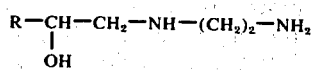
III wherein R is as hereinbefore defined. The reaction is generally carried out in an aliphatic alcohol containing 1 to 4 carbon atoms, for example ethanol or n-butanol, at a temperature between 20° C. and the boiling point of the reaction mixture.

The ethylenediamine derivatives of general formula III can be obtained by reacting ethylenediamine with an ethylene oxide of the general formula:

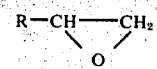
IV wherein R is as hereinbefore defined but preferably represents an optionally substituted phenyl radical, in accordance with the method of L. J. Kitchen and C. B. Pollard, J. Org. Chem., 8, 342 (1943), or with a halohydrin of the general formula:

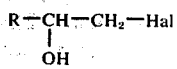
V wherein R is as hereinbefore defined but preferably represents an optionally substituted 2-, 3- or 4-pyridyl radical, and Hal represents a halogen atom, for example a chlorine or bromine atom.

The imidazo[2,1-b]thiazole derivatives prepared according to the process of the present invention are generally obtained in the racemic form and they can be resolved into their optically active isomers by application of known methods for resolving racemic forms, such as fractional crystallisation after combination with a compound which is itself optically active, e.g. di(4-toluoyl)-D-tartaric acid.

The imidazo[2,1-b]thiazole derivatives of general formula I obtained by the aforementioned process can be purified by physical methods such as distillation, crystallisation or chromatography, or by chemical methods such as the formation of salts and crystallisation of the salts and decomposition of them in an alkaline medium. In carrying out the said chemical method the nature of the anion of the salt is immaterial, the only requirement being that the salt must be well-defined and readily crystallisable.

The imidazo[2,1-b]thiazole derivatives may be converted by known methods into acid addition salts. The acid addition salts may be obtained by the action of acids on the imidazo[2,1-b]thiazole derivatives in appropriate solvents. As organic solvents there may be used alcohols, ethers, ketones or chlorinated hydrocarbons. The salt which is formed is precipitated, if necessary after concentration of the solution, and is isolated by filtration or decantation.

By the term "known methods" as used in this specification and accompanying claims is meant methods heretofore used or described in the chemical literature.

The imidazo[2,1-b]thiazole derivatives of the invention and their acid addition salts possess useful pharmacological properties. They have shown themselves to be particularly active as anti-depressants and psychoenergisers. They also possess anorexigenic properties.

In animals (rats), they have proved active at doses (p.o.) between 0.5 and 20 mg./kg. animal body weight, particularly in the following tests: antagonism of ptosis induced by tetrabenazine in accordance with the technique of M. Giurgea et al, Med. exp., 9, 249 (1963); antagonism against catalepsy induced by prochlorperazine in accordance with a technique similar to that of S. Courvoisier et al, Psychotropic Drugs, p. 373 – Elsevier Publishing Company, 1957; and potentiation of stereotypes induced by amphetamine in accordance with the technique of R. M. Quinton and G. Halliwell, Nature, 200, 178 (1963).

Of outstanding interest are those imidazo[2,1-b]thiazole derivatives of general formula I wherein R represents a phenyl radical or a phenyl radical substituted, preferably in the 3-position, by a halogen atom or an alkyl (preferably methyl) radical, an alkoxy (preferably methoxy) radical, an alkylthio (preferably methylthio) radical, or a nitro or trifluoromethyl radical, and acid addition salts thereof, and more particularly 2-phenyl-2,3,5,6-tetrahydroimidazo[2,1-b]-thiazole, 2-(3-chlorophenyl)-2,3,5,6-tetrahydroimidazo-[2,1-b]thiazole, 2-(3-fluorophenyl)-2,3,5,6-tetrahydroimidazo[2,1-b]thiazole, 2-(3-nitrophenyl)-2,3,5,6-tetrahydroimidazo[2,1-b]thiazole, 2-(3-trifluoromethylphenyl)-2,3,5,6-tetrahydroimidazo[2,1-b]thiazole, 2-(3-methoxyphenyl)-2,3,5,6-tetrahydroimidazo[2,1-b]thiazole and 2-(3-methylphenyl)-2,3,5,6-tetrahydroimidazo[2,1-b]-thiazole, and their acid addition salts.

For therapeutic purposes the imidazo[2,1-b]-thiazole derivatives of general formula I may be employed as such or in the form on non-toxic salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophylineacetates, salicylates, phenolphthalinates and methylene-bis-$\beta$-hydroxynaphthoates) so that the beneficial physiological properties inherent in the bases ane not vitiated by side-effects ascribable to the anions.

The imidazo]2,1-b]thiazole derivatives of general formula I and non-toxic acid addition salts thereof are particularly useful in the treatment of syndromes of various depressive conditions and psychasthenic conditions.

The following Examples illustrate the invention.

EXAMPLE 1

A suspension of 1-(2-hydroxy-2-phenylethyl)-imidazolidine-2-thione (44.4 g.) in hydrochloric acid ($d$ = 1.19; 100 cc.) is heated under reflux; the solid dissolves and heating is maintained for 3 hours. The solution obtained is cooled, water (500 cc.) is added and the solution is brought to pH 5 by addition of a 10N aqueous solution of sodium hydroxide (55 cc.), and is then treated with decolourising charcoal (2 g.). The aqueous phase, after addition of a 10N aqueous solution of sodium hydroxide (21 cc.), is extracted with anaesthetic grade diethyl ether (400 cc. followed by 100 cc.).

The combined organic extracts are washed with water (100 cc.), dried over sodium sulphate and concentrated under reduced pressure (30 mm.Hg). An oil (41 g.) is obtained and is dissolved in refluxing diisopropyl ether (350 cc.). On cooling, a product crystallises and is filtered off and washed with diisopropyl ether (4 × 10 cc.).

2-Phenyl-2,3,5,6-tetrahydroimidazo[2,1-b]-thiazole (28.2 g.), melting at 68°–70° C., is thus obtained.

1-(2-Hydroxy-2-phenylethyl)imidazolidine-2-thione can be obtained by the following method:

A solution of p-(2-hydroxy-2-phenylethyl)-ethylenediamine (252 g.) in ethanol (630 cc.) is added to a solution of carbon disulphide (630 cc.) in ethanol (630 cc.). A gum precipitates which is separated by decanting and dried for 30 minutes at 40° C. under reduced pressure (20 mm.Hg.). The residue thus obtained is heated gradually to 120° C. until the evolution of gas ceases. After cooling to 60° C., ethyl acetate (600 cc.) is added. A product crystallises and is filtered off and washed with ethyl acetate (3 × 50 cc.). After recrystallisation from ethanol (550 cc.), 1-(2-hydroxy-2-phenylethyl)imidazolidine-2-thione (132 g.), which melts at 127°–128° C., is obtained.

N-(2-Hydroxy-2-phenylethyl)ethylenediamine can be prepared according to L. J. Kitchen and C. B. Pollard, J. Org. Chem., 8, 342 (1943).

EXAMPLE 2

Following the procedure of Example 1 but starting with 1-[2-hydroxy-2-(4-methylthiophenyl)ethyl]-imidazolidine-2-thione (16.3 g.), there is obtained, after recrystallisation from acetonitrile, 2-(4-methylthiophenyl)-2,3,5,6-tetrahydroimidazo[2,1-b]-thiazole (10 g.) melting at 104° C.

1-[2-Hydroxy-2-(4-methylthiophenyl)ethyl]-imidazolidine-2-thione (16.3 g.) is obtained by reacting carbon disulphide (33 cc.) with N-[2-hydroxy-2(4-methylthiophenyl)ethyl]ethylenediamine (40.9 g.) in n-butanol (400 cc.); after chromatography on alumina the imidazolidine-2-thione product melts at 138° C.

N-[2-Hydroxy-2-(4-methylthiophenyl)ethyl]-ethylenediamine can be obtained by the following method:

2-(4-Methylthiophenyl)oxirane (37 g.) is added, over the course of 20 minutes and at 30° C., to a solution of ethylenediamine (75 cc.) in methanol (56 cc.). After 16 hours at 20° C., ethanol (250 cc.) is added; the precipitate which forms is filtered off. Distilled water (375 cc.) is added to the ethanol solution and the oily impurity which separates out is extracted with diisopropyl ether (200 cc.). After concentrating the aqueous ethanolic solution under reduced pressure, N-[2-hydroxy-2-(4-methylthiophenyl)ethyl]ethylenediamine (37.9 g.) is obtained in the form of an oil.

2-(4-Methylthiophenyl)oxirane can be obtained by the following method:

Sodium borohydride (4.25 g.) is added to a suspension of 2-bromo-4'-methylthio-acetophenone (73 g.) in methanol (300 cc.) kept at 8° C. The solution obtained is stirred for 1 hour at 18° C. A 1N aqueous solution of sodium hydroxide (300 cc.) and distilled water (300 cc.) are then added successively. The precipitate which forms is filtered off, washed with distilled water (2 × 30 cc.) and then dried under reduced pressure in the presence of phosphorus pentoxide. After recrystallisation from cyclohexane, 2-(4-methylthiophenyl)oxirane (36.4 g.) which melts at 48° C., is obtained.

2-Bromo-4'-methylthio-acetophenone can be prepared according to the method of R. A. Cutler et al, J. Amer. Chem. Soc., 74, 5475 (1952).

EXAMPLE 3

Following the procedure of Example 1 but starting with 1-[2-(3-chlorophenyl)-2-hydroxyethyl]-imidazolidine-2-thione (15.3 g.), 2-(3-chlorophenyl)-2,3,5,6-tetrahydroimidazo[2,1-b]thiazole (12.0 g.), melting at 80° C., is obtained.

1-[2-(3-Chlorophenyl)-2-hydroxyethyl]-imidazolidine-2-thione (27 g.), which melts at 128° C., is obtained by reacting carbon disulphide (100 cc.) with N-[2-(3-chlorophenyl)-2-hydroxyethyl]ethylenediamine (100 g.) in n-butanol (1,000 cc.).

N-[2-(3-Chlorophenyl)-2-hydroxyethyl]ethylenediamine (100 g.) is obtained in the form of an oil by reacting ethylenediamine (67 cc.) dissolved in a mixture of methanol (160 cc.) and water (50 cc.) with 2-(3-chlorophenyl)oxirane (77.0 -imidazoline-in methanol (160 cc.).

2-(3-Chlorophenyl)oxirane can be prepared in accordance with the method of R. E. Parker, J. Amer. Chem. Soc., 83, 4278 (1961).

EXAMPLE 4

Following the procedure of Example 1 but starting with 1-[2-(4-chlorophenyl)-2-hydroxyethyl]-imidazolidine-2-thione (20.8 g.), 2-(4-chlorophenyl)-2,3,5,6-tetrahydroimidazo[2,1-b]thiazole (14.5 g.), melting at 83° C., is obtained.

1-[2-(4-Chlorophenyl)-2-hydroxyethyl]-imidazolidine-2-thione (37.8 g.), which melts at 153° C., is obtained by reacting carbon disulphide (92 cc.) with N-[2-(4-chlorophenyl)-2-hydroxyethyl]ethylenediamine (80.0 g.) in n-butanol (500 cc.).

N-[2-(4-Chlorophenyl)-2-hydroxyethyl]ethylenediamine (80.0 g.) is obtained in the form of an oil by reacting ethylenediamine (63.5 cc.) dissolved in a mixture of methanol (160 cc.) and water (50 cc.) with 2-(4-chlorophenyl)oxirane (73.0 g.) dissolved in methanol (160 cc.).

2-(4-Chlorophenyl)oxirane can be prepared in accordance with the method of H. Soloway and L. Freedman, J. Amer. Chem. Soc., 80, 6062 (1958).

EXAMPLE 5

Following the procedure of Example 1 but starting with 1-[2-(3,5-dichlorophenyl)-2-hydroxyethyl]-imidazolidine-2-thione (16.6 g.), there is obtained 2-(3,5-dichlorophenyl)-2,3,5,6-tetrahydroimidazo[2,1-b]thiazole (11.8 g.). Its fumarate (14.4 g.), which melts at 233° C., is obtained by reaction of the base with fumaric acid (5 g.) in ethanol (85 cc.).

1-[2-(3,5-Dichlorophenyl)-2-hydroxyethyl]-imidazolidine-2-thione (13.6 g.), which melts at 158° C., is obtained by reacting carbon disulphide (24.8 cc.) width N-[2-(3,5-dichlorophenyl)-2-hydroxyethyl]e-thylenediamine (33.8 g.) in n-butanol (200 cc.).

N-[2-(3,5-Dichlorophenyl)-2-hydroxyethyl]-ethylenediamine (33.8 g.) is obtained in the form of an oil by reacting ethylenediamine (19 cc.) dissolved in a mixture of methanol (65 cc.) and water (20 cc.) with 2-(3,5-dichlorophenyl)oxirane (27.1 g.) dissolved in methanol (65 cc.).

2-(3,5-Dichlorophenyl)oxirane (8.6 g.) is obtained in the form of an oil, starting from 2-bromo3',5'-dichloro-acetophenone (13.5 g.), following the procedure which is described in Example 2 for the preparation of 2-(4-methylthiophenyl)oxirane.

2-Bromo-3',5'-dichloro-acetophenone can be obtained in accordance with the process of R. E. Lutz et al, J. Org. Chem., 12, 681 (1947).

EXAMPLE 6

Following the procedure of Example 1 but starting with 1-[2-(3-fluorophenyl)-2-hydroxyethyl-]imidazolidine2-thione (11.6 g.), there is obtained 2-(3-fluorophenyl)2,3,5,6-tetrahydroimidazo[2,1-b]thiazole (9 g.). Its hydrochloride (9.6 g.), which melts at 170° C., is obtained by reaction of 4.5N hydrochloric acid in anhydrous diethyl ether on the base in ethanol (25 cc.).

1-[2-(3-Fluorophenyl)-2-hydroxyethyl]-imidazolidine-2-thione (11.6 g.), which melts at 116° C., is obtained by reacting carbon disulphide (20.8 cc.) with N-[2-(3-fluorophenyl)-2-hydroxyethyl]ethylenediamine (22.9 g.) in n-butanol (230 cc.).

N-[2-(3-Fluorophenyl)-2-hydroxyethyl]ethylenediamine (22.9 g.) is obtained in the form of an oil by reacting ethylenediamine (18.4 cc.) in a mixture of methanol (25 cc.) and water (8 cc.) with 2-(3-fluorophenyl)oxirane (19.0 g.) dissolved in methanol (25 cc.).

2-(3-Fluorophenyl)oxirane (19.0 g.) is obtained in the form of an oil, starting from 2-bromo-3'-fluoro-acetophenone (34.0 g.), following the procedure which is described in Example 2 for the preparation of 2-(4-methylthiophenyl)oxirane.

2-Bromo-3'-fluoro-acetophenone (68.0 g.) is obtained in the form of an oil by reacting bromine with 3-fluoro-acetophenone (43.7 g.).

3-Fluoro-acetophenone can be obtained in accordance with the process of W. J. Horton and D. E. Robertson, J. Org. Chem., 25, 1016 (1960).

EXAMPLE 7

Following the procedure of Example 1 but starting with 1-[2-(4-fluorophenyl)-2-hydroxyethyl]imidazolidine-2-thione (9.4 g.), there is obtained 2-(4-fluorophenyl)-2,3,5,6-tetrahydroimidazo[2,1-b]thiazole (7.2 g.). Its oxalate (9.2 g.), which melts at 155° C., is obtained by reaction of the base with oxalic acid (3.2 g.) in acetone (50 cc.).

1-[2-(4-Fluorophenyl)-2-hydroxyethyl]imidazolidine-2-thione (9.6 g.), which melts at 130° C., is obtained by reacting carbon disulphide (18 cc.) with N-[2-(4-fluorophenyl)-2-hydroxyethyl]-ethylenediamine (20.0 g.) in n-butanol (220 cc.).

N-[2-(4-Fluorophenyl)-2-hydroxyethyl]ethylenediamine (20.2 g.) is obtained in the form of an oil by reacting ethylenediamine (16 cc.) dissolved in a mixture of methanol (26 cc.) and water (9 cc.) with 2-(4-fluorophenyl)oxirane (16.5 g.) dissolved in methanol (26 cc.).

2-(4-Fluorophenyl)oxirane can be obtained in accordance with the process of R. G. Pews, J. Amer. Chem. Soc. 89, 5605 (1967).

EXAMPLE 8

Following the procedure of Example 1 but starting with 1-[2-hydroxy-2-(3-nitrophenyl)ethyl]imidazolidine-2-thione (18.7 g.), there is obtained 2-(3-nitrophenyl)-2,3,5,6-tetrahydroimidazo[2,1-b]thiazole (10 g.). Its fumarate (13.4 g.), which melts at 168° C., is obtained by reaction of the base with fumaric acid (4.65 g.) in ethanol (150 cc.).

1[2-Hydroxy-2-(3-nitrophenyl)ethyl]-imidazolidine-2-thione (30.3 g.), which melts at 163° C., is obtained by reacting carbon disulphide (60 cc.) with N-[2-hydroxy-2-(3-nitrophenyl)ethyl]-ethylenediamine (75.0 g.) in n-butanol (750 cc.).

N-[2-Hydroxy-2-(3-nitrophenyl)ethyl]-ethylenediamine (76.0 g.) is obtained in the form of an oil by reacting ethylenediamine (53 cc.) dissolved in a mixture of methanol (150 cc.) and water (50 cc.) with 2-(3-nitrophenyl)oxirane (68.0 g.) dissolved in methanol (150 cc.).

2-(3-Nitrophenyl)oxirane can be obtained in accordance with the process of C. O. Guss, J. Org. Chem., 17, 681 (1952).

EXAMPLE 9

Following the procedure of Example 1 but starting with 1-[2-hydroxy-2-(4-nitrophenyl)ethyl]imidazolidine-2-thione (29.4 g.), 2-(4-nitrophenyl)2,3,5,6-tetrahydroimidazo[2,1-b]thiazole (11.0 g.), melting at 176° C., is obtained.

1-[2-Hydroxy-2-(4-nitrophenyl)ethyl]-imidazolidine-2-thione (83.8 g.), which melts at 196°–193° C., is obtained by reacting carbon disulphide (147 cc.) with N-[2-hydroxy-2-(4-nitrophenyl)ethyl]ethylenediamine (147.0 g.) in n-butanol (2,000 cc.).

N-[2-Hydroxy-2-(4-nitrophenyl)ethyl]ethylenediamine (147.0 g.) is obtained in the form of an oil by reacting ethylenediamine (100 cc.) dissolved in a mixture of methanol (250 cc.) and water (80 cc.) with 2-(4-nitrophenyl)oxirane (124.0 g.) dissolved in methanol (250 cc.).

2-(4-Nitrophenyl)oxirane can be obtained in accordance with the process of R. Fuchs and C. A. Vanderwerf, J. Amer. Chem. Soc., 76, 1634 (1954).

EXAMPLE 10

Following the procedure of Example 1 but starting with 1-[2-hydroxy-2-(3-trifluoromethylphenyl)ethyl]imidazolidine-2-thione (14.2 g.), 2-(3-trifluoromethylphenyl)-2,3,5,6-tetrahydroimidazo[2,1-b]-thiazole (10.7 g.), melting at 78° C., is obtained.

1-[(2-Hydroxy-2-(3-trifluoromethylphenyl)ethyl]imidazolidine-2-thione (14.4 g.), which melts at 117° C., is obtained by reacting carbon disulphide (20 cc.) with N-[2-hydroxy-2-(3-trifluoromethylphenyl)ethyl]ethylenediamine (27.5 g.) in n-butanol (275 cc.).

N-[2-Hydroxy-2-(3-trifluoromethylphenyl)-ethyl]ethylenediamine (28.2 g.) is obtained in the form of an oil by reacting ethylenediamine (17.3 cc.) dissolved in a mixture of methanol (28 cc.) and water (9 cc.) with 2-(3-trifluoromethylphenyl)oxirane (24.8 g.) dissolved in methanol (28 cc.).

2-(3-Trifluoromethylphenyl)oxirane (24.8 g.) is obtained in the form of an oil starting from 2-bromo-3'-trifluoromethyl-acetophenone (30.4 g.), following the process which is described in Example 2 for the preparation of 2-(4-methylthiophenyl)oxirane.

2-Bromo-3'-trifluoromethyl-acetophenone can be prepared in accordance with the process of R. M. Laird and R. E. Parker, J. Amer. Chem. Soc., 83, 4277 (1961).

EXAMPLE 11

Following the procedure of Example 1 but starting with 1-[2-hydroxy-2-(4-methoxyphenyl)ethyl]imidazolidine-2-thione (6.4 g.), 2-(4-methoxyphenyl)-2,3,5,6-tetrahydroimidazo[2,1-b]thiazole (4 g.), melting at 65°–66° C., is obtained. Its hydrochloride — obtained by reaction of 5N hydrochloric acid in anhydrous diethyl ether on the base in ethanol — melts at 210° C. after recrystallisation from ethanol.

1-[2-Hydroxy-2-(4-methoxyphenyl)ethyl]imidazolidine-2-thione (2.9 g.), which melts at 110° C., is obtained by adding a solution of N-[2-hydroxy-2-(4-methoxyphenyl)ethyl]ethylenediamine (17 g.) in ethanol (37 cc.) to a solution of carbon disulphide (37 cc.) in the same volume of ethanol. After 30 minutes, the solvent is decanted, the residue is washed with ethanol (2 × 25 cc.), n-butanol (170 cc.) is added and the mixture is heated at about 100° C. until evolution of gas ceases. Thereafter, the mixture is concentrated under reduced pressure and the residue is then recrystallised from ethanol (100 cc.).

N-[2-Hydroxy-2-(4-methoxyphenyl)ethyl]-ethylenediamine is prepared by reacting 2-(4-methoxyphenyl)oxirane (37.5 g.) dissolved in methanol (52 cc.) with ethylenediamine (30 cc.) dissolved in a mixture of methanol (52 cc.) and water (20 cc.). On distillation under reduced pressure, a product (22.3 g.), b.p. 165°–169° C./0.2 mm.Hg, is obtained, which crystallises on cooling and melts at 68° C.

2-(4-Methoxyphenyl)oxirane can be obtained in accordance with the process of R. Fuchs et al, J. Amer. Chem. Soc., 76, 1631 (1954).

EXAMPLE 12

Following the procedure of Example 1 but starting with 1-[2-hydroxy-2-(4-methylphenyl)ethyl]-imidazolidine-2-thione (8.5 g.), 2-(4-methylphenyl)-2,3,5,6-tetrahydroimidazo[2,1-b]thiazole (5.9 g.), melting at 102° C. after recrystallisation from diisopropyl ether, is obtained.

1-[2-Hydroxy-2-(4-methylphenyl)ethyl]-imidazolidine-2-thione (8.5 g.), which melts at 123° C., is obtained by reacting carbon disulphide (38 cc.) with N-[2-hydroxy-2-(4-methylphenyl)ethyl]ethylenediamine (35.4 g.) in n-butanol (150 cc.).

N-[2-Hydroxy-2-(4-methylphenyl)ethyl]-ethylenediamine (35.4 g.), b.p. 150°–156° C./0.4 mm.Hg, is obtained by reacting ethylenediamine (46.5 cc.) with 2-(4-methylphenyl)oxirane (46 g.).

2-(4-Methylphenyl)oxirane can be prepared in accordance with the process of J. Biggs et al, J. Chem. Soc. (B), p. 55 (1971).

EXAMPLE 13

Following the procedure of Example 1 but starting with 1-[2-hydroxy-2-(3-methoxyphenyl)ethyl]imidazolidine-2-thione (9.4 g.), there is obtained 2-(3-methoxyphenyl)-2,3,5,6-tetrahydroimidazo[2,1-b]thiazole (7.4 g.). Its hydrochloride (8.5 g.), which melts at 135° C., is obtained by reaction of 5N hydrochloric acid in anhydrous diethyl ether on the base in acetone (75 cc.).

Following the procedure of Example 11, 1-[2-hydroxy-2-(3-methoxyphenyl)ethyl]imidazolidine-2-thione (9.5 g.), which melts at 142° C., is obtained by reacting carbon disulphide (29.5 cc.) with N-[2-hydroxy-2-(3-methoxyphenyl)ethyl]ethylenediamine (13.6 g.).

N-[2-Hydroxy-2-(3-methoxyphenyl)ethyl]ethylenediamine (14 g.), which melts at about 50° C. (b.p. 190° C./1.5 mm.Hg), is obtained by reacting 2-(3-methoxyphenyl)oxirane (20 g.) with ethylenediamine (17.7 cc.).

2-(3-Methoxyphenyl)oxirane can be prepared in accordance with the process of J. Biggs et al, J. Chem. Soc. (B), p. 55 (1971).

EXAMPLE 14

Following the procedure of Example 1 but starting with 1-[2-hydroxy-2-(3-methylphenyl)ethyl]imidazolidine-2-thione (4.65 g.), there is obtained 2-(3-methylphenyl)-2,3,5,6-tetrahydroimidazo[2,1-b]thiazole (3.7 g.). Its fumarate (4.9 g.), which melts at 166°–167° C., is obtained by reaction of the base with fumaric acid (2.0 g.) in ethanol (50 cc.)

1-[2-Hydroxy-2-(3-methylphenyl)ethyl]-imidazolidine-2-thione (4.7 g.), which melts at 100° C., is obtained by reacting carbon disulphide (10 cc.) with N-[2-hydroxy-2-(3-methylphenyl)ethyl]-ethylenediamine (8.74 g.) in n-butanol (38 cc.).

Following the procedure of Example 11, N-[2-hydroxy-2-(3-methylphenyl)ethyl]ethylenediamine (8.74 g.), b.p. 150°–182° C./0.5–0.7 mm.Hg, is obtained by reacting ethylenediamine (14.7 cc.) with 2-(3-methylphenyl)oxirane (14.5 g.).

2-(3-Methylphenyl)oxirane can be prepared in accordance with the process of J. Biggs et al, J. Chem. Soc. (B), p. 55 (1971).

EXAMPLE 15

A mixture of 1-[2-hydroxy-2-(2-pyridyl)-ethyl]imidazolidine-2-thione (7 g.) and polyphosphoric acid (70 g.) is heated for 3 hours at 100°–110° C. The reaction mixture is cooled in an ice-water bath and is then poured into distilled water (210 cc.). The mixture is made alkaline to pH 11 by addition of aqueous sodium hydroxide solution ($d = 1.33$; 150 cc.) whilst keeping the temperature below 30° C.

The mixture is extracted with ethyl acetate (450 cc.), the extract is dried over anhydrous potassium carbonate and filtered, and the solvent is evaporated. A light brown oil (6.3 g.) is thus obtained. This oil is dissolved in ethanol (60 cc.) and decolourised by means of decolourising charcoal, and, after filtration, a 4N solution of hydrogen chloride in diethyl ether (85 cc.) is added to the filtrate. The precipitate which forms is filtered off, washed with ethanol (10 cc.) and dried under reduced pressure. 2-(2-Pyridyl)-2,3,5,6-tetrahydroimidazo[2,1-b]thiazole hydrochloride (5.4 g.) is thus obtained.

The hydrochloride is dissolved in water (12 cc.) and anhydrous potassium carbonate (3.9 g.) is added. The mixture is extracted with ethyl acetate (40 cc.) and the extracts are dried over anhydrous potassium carbonate. After filtration, the solvent is evaporated under reduced pressure (300 mm.Hg) and an oil (4 g.) is obtained which crystallises after treatment with cyclohexane (700 cc.). 2-(2-Pyridyl)-2,3,5,6-tetrahydroimidazo[2,1-b]thiazole (3.1 g.), melting at 70° C., is thus obtained.

1-[2-Hydroxy-2-(2-pyridyl)ethyl]imidazolidine2-thione can be prepared in the following way:

N-[2-hydroxy-2-(2-pyridyl)ethyl]ethylene-diamine (17 g.) is dissolved in n-butanol (170 cc.) and carbon disulphide (21.4 g.) is added to the solution. During the addition, the temperature rises from 20° to 34° C. The mixture is stirred for 15 minutes and is then heated under reflux for 30 minutes. After concentration under reduced pressure (20 mm.Hg), the residue is taken up in ethyl acetate (100 cc.). The product which crystallises is filtered off and then dried. 1-[2-Hydroxy-2-(2-pyridyl)ethyl]imidazolidine-2-thione (16 g.), which melts at 120° C., is thus obtained.

N-[2-Hydroxy-2-(2-pyridyl)ethyl]ethylene-diamine can be prepared by heating a mixture of 2-bromo-1-(2-pyridyl)ethanol (49 g.) dissolved in methanol (98 cc.), water (31 cc.) and hydrated ethylenediamine (94.5 g.), at 74° C. for 4 hours. After concentration under reduced pressure (25 mm. Hg) at 120° C., the black residue is dissolved in ethanol (350 cc.). The product which crystallises is filtered off, washed with ethanol (100 cc.) and dried under reduced pressure. N-[2-Hydroxy-2-(2-pyridyl)ethyl]ethylenediamine (32.7 g.), which melts at 144°–146° C., is thus obtained.

2-Bromo-1-(2-pyridyl)ethanol can be obtained by adding, over the course of one hour, an ice-cold solution of sodium borohydride (17.2 g.) in water (310 cc.) to a solution of 2-(2-bromoacetyl)pyridine hydrobromide (82.9 g.) in methanol (830 cc.) kept at −10° C. The mixture is allowed to return to a temperature of about 20° C. and the pH is brought to 2 by adding 48% hydrobromic acid (70 cc.). The mixture is concentrated to dryness under reduced pressure (30 mm.Hg) at a temperature below 40° C. The residue is taken up in distilled water (400 cc.) and the solution is decolourised by treatment with decolourising charcoal. The solution is brought to pH 7–8 by adding sodium bicarbonate (50 g.). The mixture is extracted with diethyl ether (1,500 cc.) and the extracts are dried over anhydrous potassium carbonate. After filtration and concentration under reduced pressure (30 mm.Hg), 2-bromo-1-(2-pyridyl)-ethanol (49 g.) is obtained in the form of an oil.

2-(2-Bromoacetyl)pyridine can be prepared in accordance with the method described by W. Wunderlich, J. Prakt. Chem., 274, 302 (1955).

EXAMPLE 16

Following the procedure of Example 15 but starting with 1-[2-hydroxy-2-(3-pyridyl)ethyl]-imidazolidine-2-thione (17 g.), 2-(3-pyridyl)-2,3,5,6-tetrahydroimidazo[2,1-b]thiazole (9.8 g.), melting at 95°–96° C., is obtained.

1-[2-Hydroxy-2-(3-pyridyl)ethyl]imidazolidine-2-thione (29.4 g.), which melts at 200°–202° C., is obtained by reacting carbon disulphide (60.5 g.) with N-[2-hydroxy-2-(3-pyridyl)ethyl]ethylenediamine (48.0 g.) in n-butanol (480 cc.).

N-[2-Hydroxy-2-(3-pyridyl)ethyl]ethylenediamine (48.0 g.) is obtained in the form of an oil by reacting ethylenediamine (212 g.) in methanol (212 cc.) with 2-bromo-1-(3-pyridyl)ethanol (110 g.) in methanol (220 cc.).

2-Bromo-1-(3-pyridyl)ethanol (110.5 g.) is obtained by reacting sodium borohydride (35.4 g.) in distilled water (635 cc.) with 3-(2-bromo-acetyl)-pyridine hydrobromide (171 g.) in methanol (1,710 cc.).

3-(2-Bromoacetyl)pyridine hydrobromide can be prepared in accordance with the method described by W. Wunderlich, J. Prakt. Chem., 274, 302 (1955).

EXAMPLE 17

Following the procedure of Example 15 but starting with 1[2-hydroxy-2-(4-pyridyl)ethyl]imidazolidine-2-thione (11.2 g.), 2-(4-pyridyl)-2,3,5,6-tetrahydroimidazo[2,1-b]thiazole (6.68 g.), melting at 98° C., is obtained.

1-[2-Hydroxy-2-(4-pyridyl)ethyl]imidazolidine-2-thione (75.2 g.), which melts at 204° C., is obtained by reacting carbon disulphide (100 cc.) with N-[2-hydroxy-2-(4-pyridyl)ethyl]ethylenediamine (100 g.) in n-butanol (100 cc.).

N-[2-Hydroxy-2-(4-pyridyl)ethyl]ethylenediamine (111 g.) is obtained by reacting ethylenediamine (315 g.) with 2-bromo-1-(4-pyridyl)ethanol (111 g.) in a mixture of methanol (576 cc.) and water (99 cc.).

2-Bromo-1-(4-pyridyl)ethanol can be prepared in accordance with the method described by L. P. Friz, Il Farmaco, Ed. Sc., 18, 972 (1963).

EXAMPLE 18

A solution of di(4-toluoyl)-D-tartaric acid (100 g.) in ethanol (1.6 liters) is added to a solution of racemic 2-phenyl-2,3,5,6-tetrahydroimidazo[2,1-b]thiazole (65 g.) (prepared as described in Example 1) in ethanol (1.7 liters). After 7 hours at 25° C., the resulting precipitate is filtered off. After two recrystallisations from methanol, (+) 2-phenyl-2,3,5,6-tetrahydroimidazo[2,1-b]thiazole di(4-toluoyl)-D-tartrate (61 g.), melting at 189° C., is obtained. On treating this salt with lithium oxide in water, there is obtained, after recrystallisation from diisopropyl ether, (+) 2-phenyl-2,3,5,6-tetrahydroimidazo[2,1-b]thiazole (18.7 g.), which melts at 98° C. and then at 108° C. after solidification $[\alpha]_D^{20} = +210.5° \pm 2.7°$ (methanol).

After the crystals have been filtered off from the solution in ethanol obtained above, the latter is concentrated under reduced pressure. After treatment with lithium oxide in water, there is obtained, following two recrystallisations from diisopropyl ether, (−) 2-phenyl-2,3,5,6-tetrahydroimidazo[2,1-b]thiazole (16 g.), which melts at 99° C. and then at 108° C. after solidification; $[\alpha]_D^{20} = -206.4° \pm 2.7°$ (methanol).

The present invention includes within its scope pharmaceutical compositions which comprise, as active ingredient, at least one imidazo[2,1-b]thiazole derivative of general formula I, or a non-toxic acid addition salt thereof, in association with a pharmaceutically-acceptable carrier or coating. The invention includes especially such preparations made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening and flavouring substances. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered orally to an adult should generally give doses between 5 and 150 mg. per day. In general, the physician will decide the posology considered appropriate, taking into account the age and weight and other factors intrinsic to the patient being treated.

The following Example illustrates pharmaceutical compositions according to the invention.

EXAMPLE 19

Tablets containing 25 mg. of active ingredient and having the following composition are prepared according to the usual technique:

| | |
|---|---|
| 2-phenyl-2,3,5,6-tetrahydroimidazo[2,1-b]thiazole | 25 mg. |
| starch | 90 mg. |
| precipitated silica | 30 mg. |
| magnesium stearate | 5 mg. |

We claim:

1. A pharmaceutical composition having antidepressant, psychoenergising and anorexigenic activity which comprises as active ingredient
an effective amount of 2-phenyl-2,3,5,6-tetrahydroimidazo[2,1-b]thiazole, or a non-toxic acid addition salt thereof,
in association with a significant amount of a pharmaceutically acceptable carrier.

* * * * *

UNITED STATES PATENT OFFICE
CERTIFICATE OF CORRECTION

Patent No. 4,005,212            Dated January 25, 1977

Inventor(s) Francois DEBARRE et al

It is certified that error appears in the above-identified patent and that said Letters Patent are hereby corrected as shown below:

Under the heading "[30] Foreign Application Priority Data", the date of the second priority document should be changed from "Nov." to read --Oct.--

Signed and Sealed this

Thirty-first Day of May 1977

[SEAL]

Attest:

RUTH C. MASON
Attesting Officer

C. MARSHALL DANN
Commissioner of Patents and Trademarks